United States Patent

Maharaj et al.

[11] Patent Number: 6,004,277
[45] Date of Patent: Dec. 21, 1999

[54] PERSONAL PULMONARY FUNCTION ANALYZERS

[76] Inventors: Prashant Desmond Maharaj, 168 Showground Road, Castle Hill, NSW 2154; Donald Lewis Butler, 176 Fox Valley Road Suite 10, Wahroonga, NSW 2076, both of Australia

[21] Appl. No.: 08/973,134
[22] PCT Filed: Jun. 3, 1996
[86] PCT No.: PCT/AU96/00333
  § 371 Date: Feb. 13, 1998
  § 102(e) Date: Feb. 13, 1998
[87] PCT Pub. No.: WO96/38084
  PCT Pub. Date: Dec. 5, 1996
[30] Foreign Application Priority Data Jun. 1, 1995 [AU] Australia .................. PN3322

[51] Int. Cl.$^6$ .................................................. A61B 5/08
[52] U.S. Cl. ................................. 600/538; 600/532
[58] Field of Search .................. 600/538, 529, 600/532, 533, 543, 300, 301

[56] References Cited

U.S. PATENT DOCUMENTS

| 3,848,584 | 11/1974 | Otsap ....................... 600/538 |
| 4,736,750 | 4/1988 | Valdespino ................ 600/538 |
| 4,768,520 | 9/1988 | Varraux ..................... 600/538 |
| 4,905,709 | 3/1990 | Bieganski ................. 600/538 |
| 5,058,601 | 10/1991 | Riker ........................ 600/538 |
| 5,170,798 | 12/1992 | Riker ........................ 128/725 |

FOREIGN PATENT DOCUMENTS

| 0 437 055 A1 | 7/1991 | European Pat. Off. . |
| WO 86/01172 | 2/1986 | WIPO . |
| WO 87/01443 | 3/1987 | WIPO . |
| WO 92/15246 | 9/1992 | WIPO . |

*Primary Examiner*—Cary O'Connor
*Assistant Examiner*—Navin Natnithithadha
*Attorney, Agent, or Firm*—Townsend and Townsend and Crew LLP

[57] ABSTRACT

A personal pulmonary function analyzer comprises a generally elongate body which defines a flow passageway extending between an opening at one end of the body and an opening at a side of the body. The flow passageway can be less than 10 cm in length, and is conveniently about 3 cm in length.

14 Claims, 5 Drawing Sheets

PERSONAL PULMONARY FUNCTION ANALYZERS

TECHNICAL FIELD

The invention relates to personal pulmonary function analyzers, and particularly to pulmonary function analyzers which are sufficiently portable to be carried by a user.

BACKGROUND OF THE INVENTION

Lung function depends on the ease with which air passes from the atmosphere to the alveoli (air sacs) and back to the atmosphere again. This is mainly determined by the flow resistance of the small airways of the lungs. Lung function can vary considerably over short periods of time, and can be affected by such factors as temperature, humidity, exercise and disease, such as asthma. For example, a person playing a sport may suddenly become short of breath as a result of a sport-induced bronchiospasm, in which the bronchial tubes contact due to exertion. Asthma sufferers are also particularly vulnerable to allergens, viruses and smoke.

Although portable peak-flow meters are available at low price, their usefulness in analyzing lung function is limited. Such peak-flow meters are prone to significant errors, which are particularly undesirable in the case where the meters are used to regulate a drug treatment for a pulmonary disorder. Known low price peak-flow meters are based on mechanical friction spring arrangements, which are uncalibrated, and intended to provide relative results only. Such devices are often used to regulate a user's intake of steroids, which provide a preventative treatment for asthma. It will be appreciated that an incorrect reading from the peak-flow device will result in the user's taking an incorrect dose of steroids, either too much or too little, which is undesirable and potentially dangerous.

In order to carry out accurate pulmonary function tests, it is normally necessary for the patient's lung function to be tested in the hospital using non-portable testing equipment. However, in view of the fact that asthma, particularly in the case of asthma suffers who are children, is believed often to contain a psychosomatic element, tests which are carried out in the hospital do not always give representative results. This is because the mere fact that a patient has to attend the hospital tends to increase the stress level of the patient, and this in turn leads to less reliable test results. Lung function is very changeable over short periods of time, e.g. before and during exercise. To get a complete picture of a person's lung function, multiple measurements over time need to be taken during normal day-to-day activities. At present, testing a patient in the hospital is often the only way of carrying out the full range of appropriate tests.

Such tests result in a variety of useful measurements, the five most significant of which are summarized below.

PEAK FLOW is the simplest measurement, and is simply an indication of the peak velocity of expelled air expressed in liters per minute. This measurement, like the other measurements discussed below, is typically obtained by asking the patient to blow into suitable apparatus.

VC is the total volume of expelled air, expressed in liters.

FEV1 is the volume of air expelled in the first second, expressed in liters.

FEV1/VC is the volume of air expelled in the first second divided by the total volume expelled, expressed as a percentage.

FEF25%–75% is the average velocity of air flow between 25% expelled volume and 75% expelled volume, expressed in liters per minute.

Devices for carrying out the above measurements typically involve the patient's blowing through a tube containing a restriction, and taking pressure measurements on each side of the restriction. The restriction is often in the form of one or more gauzes or meshes, which have the effect of reducing the chaotic behavior of the air flow through the pipe. A portable device which operates on the basis of pressure measurements on either side of a flow restriction is described in Australian Patent Application No. 67994/90. FIG. 1 of that application shows a hand-held device (see FIG. 1), the upper part of which is provided with a straight tube 16 along which the user blows air in order to obtain PEAK FLOW and FEV1 measurements. These measurements are obtained by measuring the pressure on either side of a restriction within the tube 16, as shown in FIG. 5. Although the device is portable, the device cannot easily be carried in a pocket. This is due in part to the length of the tube 16 of the manufactured article, which is around 12 cm. In the prior art, lengths of this size or greater have been favored in order to reduce the chaotic behavior of the air flow within the tube, thus making reliable pressure measurements within the tube more easy to carry out.

The invention seeks to provide an improved personal pulmonary function analyzer, and an improved method of performing flow measurements in a personal pulmonary function analyzer.

DISCLOSURE OF INVENTION

According to the invention there is provided a personal pulmonary function analyzer comprising a generally elongate body which defines a flow passageway extending between a first opening at one end of the body and a second opening at a side of the body, wherein the flow passageway extends along a curve between the first and second openings, and wherein the second opening opens directly to the atmosphere.

It will be appreciated that, because the flow passageway does not pass along the whole length of the body, the body is able to be made more compact.

Advantageously, there are no obstructions within the flow passageway other than a pressure measurement tube. This is convenient as it allows the flow passageway to be easily cleaned, and has minimum effect on the flow of air through the passageway.

The invention also provides a method of measuring the flow rate within the flow passageway of a personal pulmonary function analyzer, the method comprising measuring the pressure at a location within the flow passageway, measuring the ambient air pressure around the analyzer, and comparing the two pressure measurements, the method being carried out in a personal pulmonary function analyzer as described above.

BRIEF DESCRIPTION OF THE DRAWINGS

Embodiments of the invention will now be more particularly described, by way of example only, with reference to the accompanying drawings, in which.

BEST MODE FOR CARRYING OUT THE INVENTION

Figure 1:
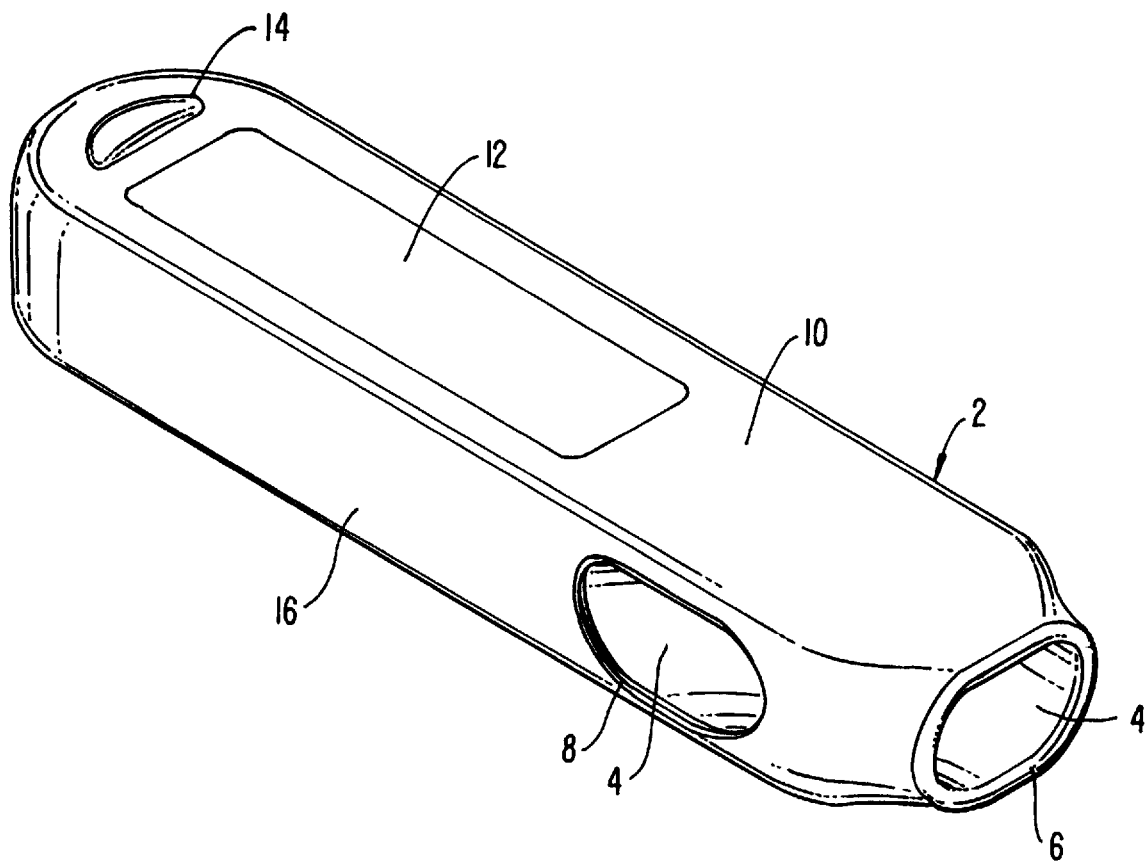
FIG. 1 is a perspective view of the body of a personal pulmonary function analyzer in accordance with the invention.

The body 2 of the personal pulmonary function analyzer is shown in FIG. 1, and defines a flow passageway 4 which extends between an input opening 6 and an output opening 8. The body 2 is elongate, and has an upper surface 10 provided with a transparent window 12 and a button 14. An LCD (not shown) is located below the window 12, and provides a readout of the various measurements which can be carried out using the analyzer. The operation of the button 14 will be described below. The window 12 and button 14 are sealed, so that the entire analyzer can be submerged under water without damage, The input opening 6 is located at the opposite end of the body 2 to the button 14, and the flow passageway 4 is curved so that the output opening 8 is located on a side wall 16 of the body 2.

It will be appreciated that such a design allows the pulmonary function analyzer to be considerably reduced in size, in view of the fact that the flow passageway 4 passes through only a small portion of the body 2. Hitherto, it has been thought necessary to provide as straight a flow passageway as possible in order to reduce the chaotic-behavior of the air flow within the passageway. Various other measures, such as the gauzes and meshes described above, were also employed in the prior art in order to reduce chaotic behavior. The provision of a curved flow passageway 4 therefore represents a significant departure from current thinking in the art.

Furthermore, the length of the flow passageway 4, measured along the center of the flow passageway 4, is only about 3 cm. Such a short flow passageway 4 results in some chaotic behavior of the air in the passageway 4. However, it has been found that the resulting variations in pressure measurements within the flow passageway 4 can be overcome by filtering and averaging the pressure samples using appropriate software.

Figure 2:
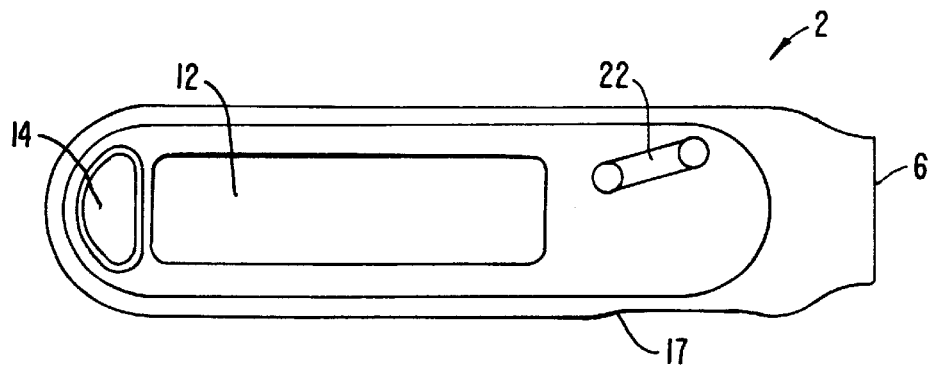
FIG. 2 is a plan view of the upper side of the upper part of the body.
Figure 3:
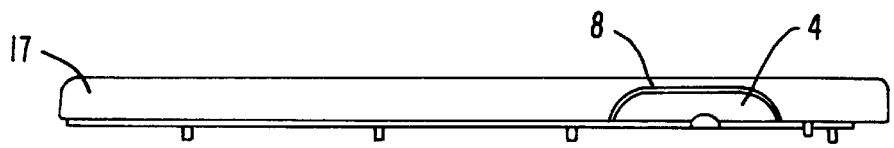
FIG. 3 is a side view of the upper part.
Figure 4:
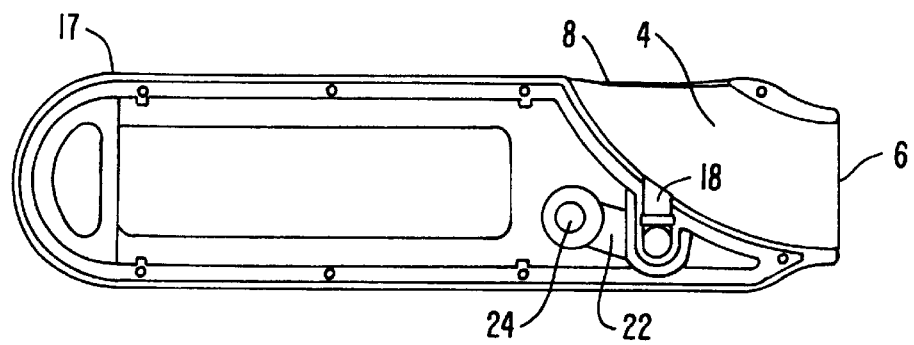
FIG. 4 is a plan view of the lower side of the upper part.
Figure 5:
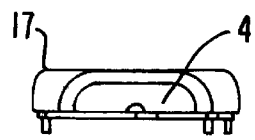
FIG. 5 is an end view of the upper part.

The body 2 is formed from an upper part 17, shown in FIGS. 2 to 5, and a lower part, shown in FIGS. 6 to 9. Referring to FIG. 4, the upper part defines the upper half of the flow passageway 4, together with the upper half of a tube socket 18. The tube socket 18 is adapted to hold a flow measurement tube 20 shown in FIG. 10. The tube socket 18 opens at one end into the flow passageway 4, and opens at the other end into a conduit 22, which is in turn connected to a pressure transducer opening 24. When the analyzer is assembled, the opening 24 opens onto one side of a solid state pressure transducer (not shown). The conduit 22 is also visible as a protrusion on the upper side of the upper part, as shown in FIG. 2.

Figure 6:
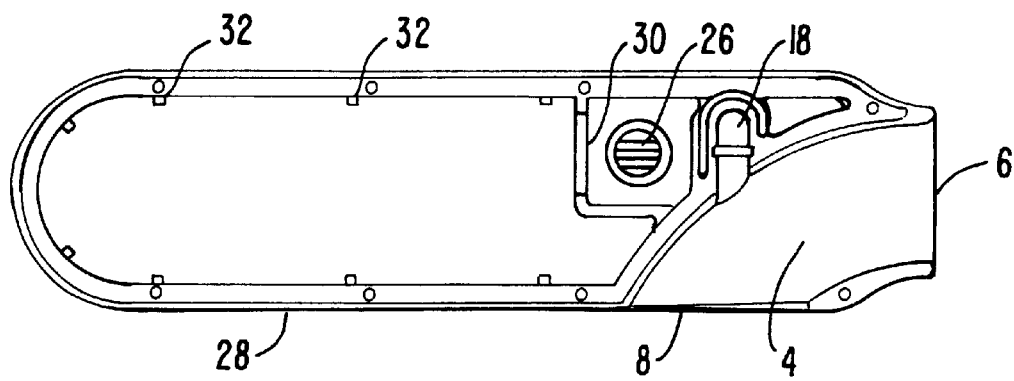
FIG. 6 is a plan view of the upper side of the lower part of the body.
Figure 7:
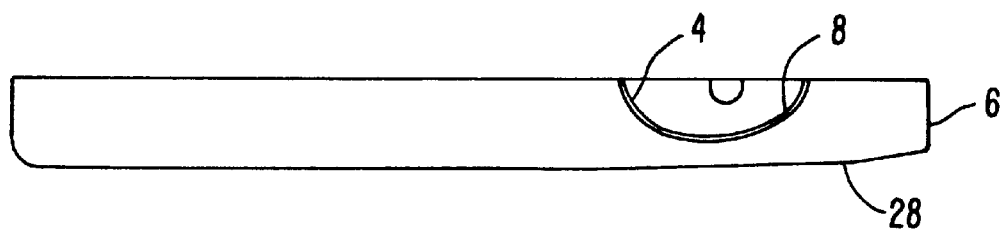
FIG. 7 is a side view of the lower part.
Figure 8:
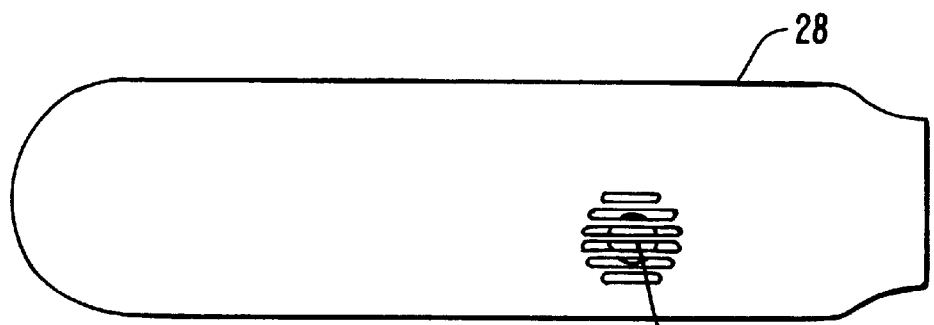
FIG. 8 is a plan view of the lower side of the lower part.
Figure 9:
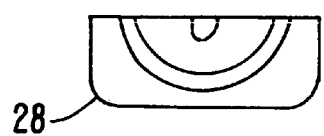
FIG. 9 is an end view of the lower part.

The other side of the solid state pressure transducer is exposed to ambient air pressure via a grilled opening 26 in the lower part 28 of the body 2. as shown in FIG. 8. The lower part 28 defines the lower part of the flow passageway 4 and the lower part of the tube socket 18, as shown in FIG. 6 The lower part 28 also defines an enclosure 30 within which the solid state transducer is housed. A number of prorusions 32 are also provided to support the PCB (not shown) which sits below the transparent window 12 as described above, arid on which the LCD is mounted.

Figure 10:
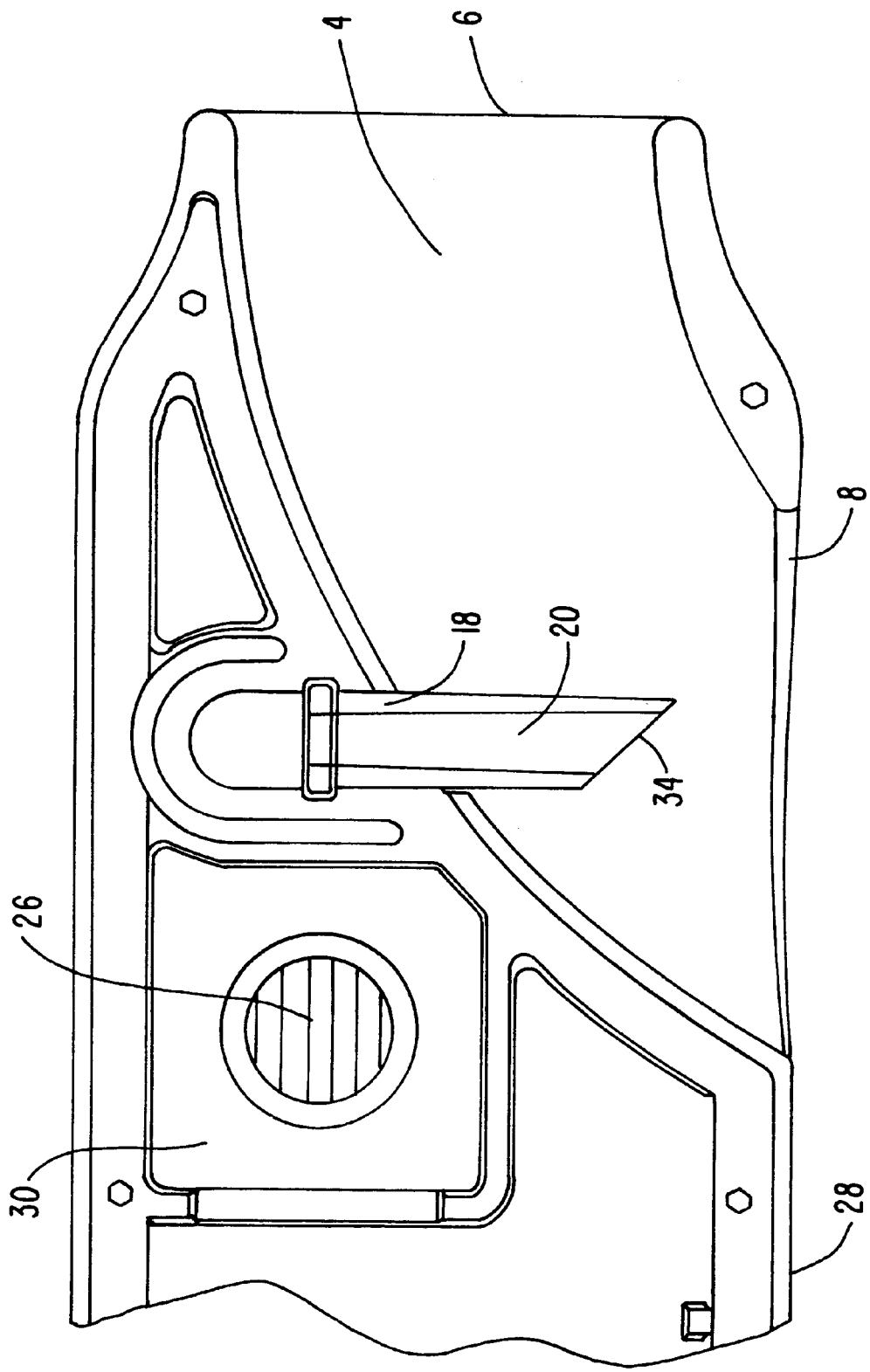
FIG. 10 is an enlarged view of the flow passageway region of the lower part shown in FIG. 6.

FIG. 10 is an enlargement of a portion of FIG. 6. The flow measurement tube 20 is directed generally perpendicular to the longitudinal axis of the body 2, and projects from the socket 18 into the flow passageway 4. The tube 20 is cylindrical, and provided with a slanted opening 34 at one end thereof. The opening 34 is thus directed in the downstream direction of the flow passageway 4 so that when the user blows into the input opening 6 a vacuum or low pressure region is produced adjacent the opening 34. The vacuum is passed to the solid state pressure transducer via the conduit 22, and a comparison is made with the ambient pressure.

The operation of the personal pulmonary function analyzer will now be described with reference to the flow diagram shown in FIG. 11.

At step 1, the button 14 is pressed, and a microcontroller (not shown) within the body 2 is supplied by internal lithium cells with enough power to switch on. The microcontroller is a conventional device, which contains its own RAM and ROM.

At step 2, the microcontroller is initialized, and its registers are reset, as are data values. Processor speed and periodic interrupt information is set. The periodic interrupt occurs 100 times per second, which is thus the sampling rate of the device.

At step 3, the pulmonary function analyzer calibrates itself by taking 50 pressure samples, and filtering these samples using appropriate software to produce a running average of the samples. The pressure in the flow passageway 4 when the user is not blowing through the flow passageway 4 is therefore sampled 50 times in order to produce a zero reference pressure. The zero reference pressure is simply the running average result of the 50th sample.

At step 4, the LCD displays, through the window 12, the word READY, and the analyzer then enters a loop 5 in which the pressure in the flow passageway 4 is sampled 100 times per second in order to detect whether the user is blowing into the input opening 6. The threshold for this detection is chosen to be any suitable pressure measurement in excess of the zero reference calculated in step 3. In the present embodiment, a value of two sample points is used as the trigger. That is, the pressure detected by the flow measurement tube 20 must increase by two of the smallest units which the device can measure in order to exceed the threshold.

Figure 11:
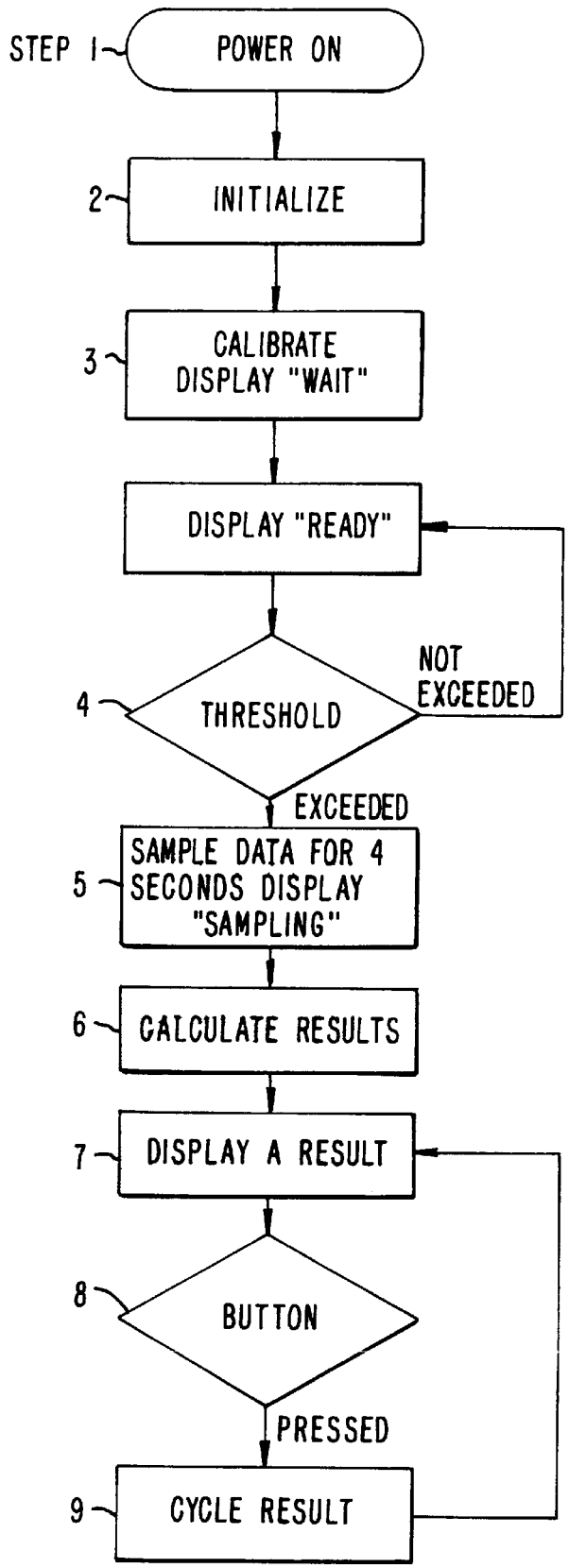
FIG. 11 is a flow diagram showing the basic operation of the analyzer.

Once the threshold has been exceeded, as a result of the user blowing into the flow passageway 4, the pressure in the flow passageway 4 is sampled every 100th of a second for four seconds, as shown in step 6 of FIG. 11. The sampled values are stored in the memory of the device, and filtered using appropriate software.

At step 7, sampling of the pressure in the flow passageway 4 is stopped (thus saving battery power), and the results are calculated by the microcontroller. The microcontroller is able to calculate the five pulmonary measurements described above, namely, PEF25%–75%, FEV1, PEAK FLOW, VC and FEV1/VC. One of the those quantities is displayed through window 12 at step 8, and each press of the button 14 (step 9) causes the next quanuty to be displayed through the window 12.

At any time, if button 14 is held down for more than 1.5 seconds, the unit is reset, and the above process is restarted.

In order to preserve the battery, the unit automatically switches off after about 12 seconds of idle time.

The foregoing describes only preferred embodiments of the present invention, and modifications, obvious to those skilled in the art, can be made thereto without departing from the scope of the present invention.

We claim:

1. A personal pulmonary function analyzer comprising a generally elongate body having two ends and a side extending between said two ends, a flow passageway extending between a first opening located at one said end of the body and a second opening located at said side of the body intermediate said two ends, the flow passageway extending along a curve between the first and second openings, the second opening directly to the atmosphere, and passageway pressure measurement means extending at least partially into said curved flow passageway for measuring the pressure within said curved flow passageway.

2. A personal pulmonary function analyzer as claimed in claim 1, wherein said first opening of the flow passageway, at said end of the body, is an input opening into which a user blows when using the analyzer.

3. A personal pulmonary function analyzer as claimed in claim 1, wherein the flow passageway is smoothly curved between said first and second openings.

4. A personal pulmonary function analyzer as claimed in claim 3, wherein the flow passageway is smoothly curved between said first and second openings along most of the length of the flow passageway.

5. A personal pulmonary function analyzer as claimed in claim 3, wherein the flow passageway is smoothly curved between said first and second openings along the whole of the length of the flow passageway.

6. A personal pulmonary function analyzer as claimed in claim 1, wherein the analyzer further comprises pressure comparison means connected to said passageway pressure measurement means for comparing said pressure within the flow passageway with the ambient air pressure around the analyzer.

7. A personal pulmonary function analyzer as claimed in claim 1, wherein the passageway pressure measurement means comprises a tube which extends into the flow passageway, and which has a passageway opening at the end thereof which opens into the flow passageway.

8. A personal pulmonary function analyzer as claimed in claim 7, wherein said passageway opening is slanted with respect to the tube so as to face in the downstream direction of the flow passageway.

9. A personal pulmonary function analyzer as claimed in claim 7, wherein there are no obstructions within the flow passageway other than the tube.

10. A personal pulmonary function analyzer as claimed in claim 1, wherein the flow passageway is not more than 10 cm in length.

11. A personal pulmonary function analyzer as claimed in claim 10, wherein the length of the flow passageway is less than 7.5 cm.

12. A personal pulmonary function analyzer as claimed in claim 10, wherein the length of the flow passageway is less than 5 cm.

13. A personal pulmonary function analyzer as claimed in claim 10, wherein the length of the flow passageway is around 3 cm.

14. A method of measuring the flow rate within the flow passageway of a personal pulmonary function analyzer which includes a generally elongate body having two ends and a side extending between said two ends, a flow passageway extending between a first opening located at one said end of the body and a second opening located at said side of the body intermediate said two ends, the flow passageway extending along a curve between the first and second openings, the second opening opening directly to the atmosphere, the method comprising measuring the pressure at a location within the curved flow passageway, measuring the ambient air pressure around the analyzer, and comparing the two pressure measurements.

\* \* \* \* \*